United States Patent [19]

Stiles et al.

[11] Patent Number: 5,433,712
[45] Date of Patent: Jul. 18, 1995

[54] SELF-SHEATHING HYPODERMIC SYRINGE

[75] Inventors: Donald E. Stiles, 5860 McCoin Dr., Dryden, Mich. 48428; Randall M. Brakeman, 27390 Wellington, Franklin, Mich. 48025; Dewayne J. Sherwin, 378 S. Sommers Rd., Imlay City, Mich. 48444

[73] Assignees: Donald E. Stiles, Dryden; Randall M. Brakeman, Franklin, both of Mich.

[21] Appl. No.: 74,931

[22] Filed: Jun. 10, 1993

[51] Int. Cl.⁶ ............................................. A61M 5/32
[52] U.S. Cl. .................................. 604/197; 604/110; 604/198; 604/195
[58] Field of Search ............... 604/197, 198, 192, 263, 604/187, 227, 195, 110, 218, 236, 207–211, 234, 220, 240–243

[56] References Cited

U.S. PATENT DOCUMENTS

| | | |
|---|---|---|
| 5,026,346 | 6/1991 | Spanner et al. |
| 5,053,018 | 10/1991 | Talonn et al. ............... 604/198 |
| 5,057,079 | 10/1991 | Tiemann et al. ............. 604/110 |
| 5,066,281 | 11/1991 | Stevenson-Mitchener . |
| 5,088,988 | 2/1992 | Talonn et al. . |
| 5,120,310 | 6/1992 | Shaw . |
| 5,135,510 | 8/1992 | Maszkiewicz et al. ....... 604/195 |

*Primary Examiner*—John D. Yasko
*Assistant Examiner*—V. Alexander
*Attorney, Agent, or Firm*—Remy J. VanOphem; John VanOphem

[57] ABSTRACT

A hypodermic syringe assembly which is self-sheathing in that use of the syringe activates a locking mechanism which automatically and irreversibly causes a hypodermic needle to be retracted into an outer sheath. As a result, the syringe assembly is automatically and permanently made safe to handle by the user. In addition, reuse of the syringe is prevented by the locking mechanism, in that the locking mechanism serves to puncture the syringe if an attempt is made to reuse the syringe. The syringe includes a tubular-shaped sheathing member having an apertured end through which the hypodermic needle extends when the syringe is in use. Telescopically disposed within the sheathing member is a tubular-shaped insert having one end which is open to receive a plunger, with the other end being provided with an aperture and boss for receiving the hypodermic needle. As assembled, the insert is retained in a first position relative to the sheathing member, such that the hypodermic needle projects through the apertured end of the sheathing member. The insert is biased toward a second position relative to the sheathing member, whereby the hypodermic needle is retracted within the sheathing member. The locking mechanism permits the insert to shuttle to the second position at the end of the injection procedure, and is activated by a camming member which is rotatably supported on the insert adjacent the plunger end of the syringe.

18 Claims, 3 Drawing Sheets

SELF-SHEATHING HYPODERMIC SYRINGE

BACKGROUND OF THE INVENTION

1. Field of the Invention

The present invention generally relates to hypodermic syringes used to inject medications and/or vaccines into the body of a human or animal. More specifically, this invention relates to a hypodermic syringe which is self-sheathing, such that the hypodermic needle is automatically and irreversibly retracted into a sheath after the contents of the syringe are dispensed, so as to prevent the needle from accidentally scratching or cutting the user or others, as well as to prevent the reuse of the syringe.

2. Description of the Prior Art

Hypodermic syringes are well known for their use in the dispensing of medication and vaccines for various types of medical treatment. Hypodermic syringes generally include a syringe body or barrel, a hypodermic needle secured to one end of the syringe barrel, and a plunger reciprocably received in the opposite end of the syringe barrel. The hypodermic needle is a hollow tube with a sharp point which enables the needle to penetrate the skin and muscle of the subject.

After its use, a hypodermic syringe poses a hazard unless and until the hypodermic needle has been removed or covered to prevent accidentally scratching or cutting the user or others. This hazard is particularly serious because of the risk of accidentally communicating a highly infectious disease, such as hepatitis B or acquired immune deficiency syndrome. Though health care workers are particularly at risk in that they are regularly exposed to the hazards posed by used hypodermic syringes, the misuse of discarded hypodermic syringes by intravenous drug users is also a notable problem, particularly in the spread of acquired immune deficiency syndrome.

Consequently, numerous types of hypodermic syringes which can be readily disabled have been suggested by the prior art. Generally, each attempts to retract the hypodermic needle into a sheath or into the barrel of the syringe, or provide a shield which can be extended to cover the needle after the syringe has been used, The prior art syringes differ primarily in the type of mechanism by which the shield is deployed and the manner in which the needle is prevented from being re-exposed. As an example, U.S. Pat. No. 5,135,510 to Maszkiewicz et al. discloses a syringe whose needle can be retracted into a protective sheath by operating a trigger which disengages a ratchet mechanism. Another example of a manually-operated retract mechanism is taught by U.S. Pat. No. 5,066,281 to Stevenson-Michener, wherein the needle is retracted after use by pulling back on the syringe barrel until the needle is drawn into a sheath, and the plunger is then rotated to permanently lock the barrel and plunger, such that the needle cannot be re-extended outside of the sheath. A further example is a cam-operated locking mechanism taught by U.S. Pat. No. 5,088,988 to Talonn et al., which makes possible a relatively small syringe suitable for use by dentists.

However, a disadvantage which the above nonreusable syringes have in common is that the user must be relied upon to disable the syringe after its use in order for the safety feature to be activated. Also, the ratchet mechanism taught by Maszkiewicz et al. can be readily defeated by disengaging the mating members of the ratchet mechanism. A disadvantage with the syringe taught by Stevenson-Michener is that visual observation of the syringe does not indicate whether the syringe has been disabled. In addition, a disadvantage with the syringe taught by Talonn et al. is the complexity of a locking collar which serves to disable the syringe, making the syringe more difficult to manufacture.

Other examples of nonreusable syringes taught by the prior art include U.S. Pat. No. 5,120,310 to Shaw, which relies on the elastic property of the syringe barrel to serve as a locking and release mechanism for the hypodermic needle. When released, the hypodermic needle is automatically retracted into the syringe barrel to provide the disabling function for the syringe. Though the syringe taught by Shaw has an advantage in that it is automatically disabled after all the fluid has been dispensed from the syringe, its operation relies on the user generating a force sufficient to overcome the gripping strength of the syringe, a characteristic based on properties of the syringe which may be difficult to control in mass production. In addition, the syringe taught by Shaw requires additional components disposed within the syringe barrel, which reduces the relative capacity of the syringe for a given size, as well as contributes additional sources for contamination of the contents of the syringe. Furthermore, the entire contents must be dispensed from the syringe taught by Shaw before the locking mechanism is activated.

In contrast, U.S. Pat. No. 5,026,346 to Spanner et al. employs a disabling device which is automatic and does not require dispensing the entire contents of the syringe barrel to activate the disabling mechanism. However, Spanner et al. involves a rather complicated construction which operates to break the seal on the plunger, so as to prevent subsequent refilling of the syringe.

While the above examples represent only a fraction of the syringes taught by the prior art, they serve to highlight some of the more common disadvantages associated with the use of known nonreusable syringes. Generally, from the above discussion, it can be readily appreciated that the prior art does not teach within a single disclosure a nonreusable syringe which 1) does not rely upon the user to manually disable the syringe after its use; 2) does not require a complicated locking mechanism; 3) does not rely on a locking mechanism which can be easily defeated; 4) does not require the entire contents of the syringe to be used before the syringe can be disabled; 5) does not require close inspection to determine whether the syringe has been disabled; and 6) does not significantly reduce the fluid capacity of the syringe.

Accordingly, what is needed is a cost-efficient, readily manufacturable syringe assembly which employs an uncomplicated locking mechanism that visibly renders the syringe unusable, wherein the locking mechanism is activated prior to the use of the syringe, such that any subsequent use of the syringe results in the permanent disablement of the syringe.

SUMMARY OF THE INVENTION

According to the present invention there is provided a hypodermic syringe assembly for dispensing medication, vaccines and the like. The syringe assembly is self-sheathing in that use of the syringe activates a locking mechanism that automatically and irreversibly causes the hypodermic needle to be retracted into an outer protective sheath. As a result, the syringe assembly is immediately made safe to handle by the user, and the syringe is disabled such that reuse is prevented.

The syringe assembly of this invention includes a tubular-shaped sheathing member having an apertured end. Telescopically disposed within the sheathing member is a tubular-shaped insert having one end which is open to receive a plunger, with the other end being provided with an aperture adapted to receive and secure a hypodermic needle. The insert serves as the barrel of the syringe in which the medication or vaccine is contained prior to injection.

As assembled, the insert is locked in a first position relative to the sheathing member with a first locking member, such that the hypodermic needle is deployed through the apertured end of the sheathing member. As a result, with the insert locked in the first position, the syringe assembly is ready for immediate use. However, the insert is biased toward a second position relative to the sheathing member, such that the hypodermic needle would be retracted into the sheathing member if the first locking member were disengaged.

To activate the safety mechanism of the syringe assembly which prevents its reuse, the syringe assembly also includes a camming member rotatably supported on the insert. The camming member has a release feature which is selectively engagable with the first locking member to disengage the first locking member, such that the insert is urged toward the second position. The camming member further includes a camming contour which limits the operation of the camming member between a null position and an activated position, in which the first locking member is disengaged by the release feature on the camming member. As a result, if the syringe assembly is released by the user, the insert is shuttled to its second position in which the hypodermic needle is retracted within the sheathing member. Once the hypodermic needle is retracted, a second locking member prevents the forward movement of the insert relative to the sheathing member, such that the hypodermic needle is prevented from being re-deployed through the apertured end of the sheathing member.

The camming member preferably has its axis of rotation coincident with the longitudinal axis of the insert and sheathing member so as to more readily integrate the camming member with the construction of a conventional syringe assembly. To further streamline the construction of the syringe assembly of this invention, the camming member resides primarily between the sheathing member and the insert, with only a radially extending shoulder being exposed to permit the operation of the camming member by the user. Consequently, the camming member is unobtrusive to the user during the use of the syringe assembly.

According to a preferred aspect of this invention, the syringe assembly is provided ready for use, with the user being required only to install the hypodermic needle, if not pre-installed. The insert can be filled with the desired medication or vaccine in a substantially conventional manner by drawing back on the plunger within the insert until the desired quantity of fluid has accumulated within the insert. Then, by rotating the camming member, the first locking member is disengaged such that, if released, the hypodermic needle would be retracted into the sheathing member as a result of the insert being urged toward its second position relative to the sheathing member. However, this force is sufficiently low such that, with the syringe assembly in hand, the user can readily inject the fluid in a completely normal manner.

Once the user has released the plunger at the end of the procedure, the insert is immediately urged toward its second position relative to the sheathing member, such that the hypodermic needle is completely and safely withdrawn into the sheathing member. Thereafter, the second locking member prevents the insert from being repositioned to its first position, by which the hypodermic needle would be redeployed through the apertured end of the sheathing member.

Accordingly, a significant advantage of the present invention is that use of the syringe assembly is substantially conventional, other than the requirement to rotate the camming member prior to injection. Because this step is performed prior to inserting the needle into the subject, the user is not significantly inconvenienced. Once properly indexed, the insert will retract the needle into the sheathing member by nothing more than the user releasing the syringe. Accordingly, the user is not required to physically disable the syringe assembly after its use, and can immediately tend to the needs of the recipient of the injection.

In addition, a significant advantage of the present invention is that the syringe assembly employs an uncomplicated locking mechanism which cannot be easily defeated, and does not require the entire contents of the syringe to be used before being disabled. Furthermore, the syringe assembly can quickly be identified as being disabled by a casual visual inspection.

Another advantage is that the insert is a substantially conventional syringe barrel, such that the internal capacity of the insert is not reduced by the mechanisms required to disable the syringe. Accordingly, the size of the syringe assembly can be minimized for a given desired capacity. Furthermore, avoiding the use of components within the insert avoids the introduction of additional sources of contamination within the syringe assembly.

Accordingly, it is an object of the present invention to provide a nonreusable syringe assembly which includes a safety feature that protects the user and others from the syringe's hypodermic needle following the use of the syringe.

It is a further object of the invention that the syringe assembly employ a disabling mechanism which automatically and permanently withdraws the hypodermic needle into a protective sheath, so as to prevent the user from being accidentally scratched or cut with the needle.

It is still a further object of the invention that the syringe assembly employ a locking mechanism which cannot be readily defeated, such that activation of the disabling mechanism will result in a syringe assembly which is made nonreusable.

It is another object of the invention that the syringe assembly employ an uncomplicated camming mechanism which serves to activate the locking mechanism.

It is yet another object of the invention that the camming mechanism be incorporated within the syringe assembly so as not to be obtrusive to the user and an impediment to the use of the syringe assembly.

It is still another object of the invention that the syringe assembly be visibly disabled after its use.

Other objects and advantages of this invention will be more apparent after a reading of the following detailed description taken in conjunction with the drawings provided.

DETAILED DESCRIPTION OF THE PREFERRED EMBODIMENT

Figure 1:
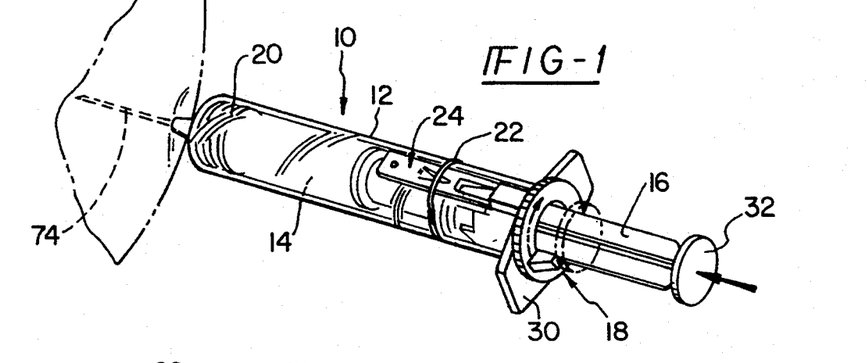
FIG. 1 is a perspective view of a self-sheathing syringe assembly in an operational mode in accordance with the preferred embodiment of this invention.
Figure 2:
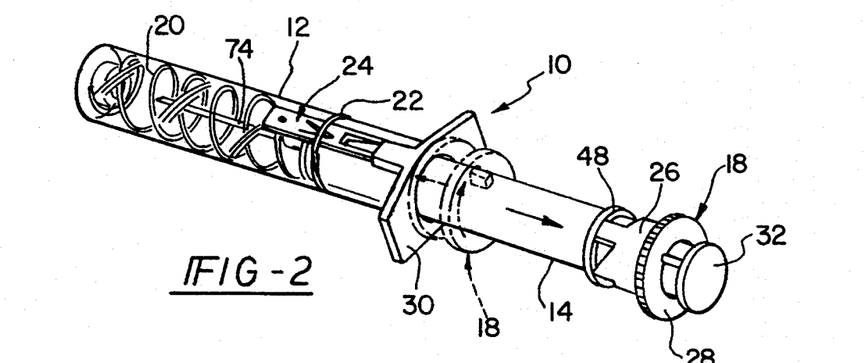
FIG. 2 is a perspective view of the self-sheathing syringe assembly of FIG. 1 in a disabled mode in accordance with the preferred embodiment of this invention.

With reference to FIGS. 1 and 2, there is shown a self-sheathing hypodermic syringe 10 which is suitable for injecting a medication, vaccine or the like. FIG. 1 illustrates the appearance of the syringe 10 in an operational mode during an injection procedure, while FIG. 2 illustrates the appearance of the syringe 10 in a disabled mode immediately following the injection procedure, wherein the syringe 10 has been permanently disabled to prevent further use. As seen in FIGS. 1 and 2, except for a camming member 18 disposed at one end of the syringe 10, the syringe 10 is substantially conventional in appearance. As is conventional, the syringe 10 includes a hypodermic needle 74, a plunger or piston member 16 having a flange 32 against which the user presses to dispense the contents within the syringe 10, and a pair of finger flanges 30 which can be used by the user as leverage while the plunger 16 is being depressed. However, what appears to be the barrel of the syringe 10 is a sheath 12 which serves to house the hypodermic needle 74 after the user has dispensed the contents of the syringe 10.

Additional external features which are not conventional include a snap ring 22 fitted around the circumference of the sheath 12, and a locking member 24 secured to the sheath 12. Internally, a spring 20 and syringe barrel or outer tube 14 are shown. The barrel or outer tube 14 contains the medication to be injected into a subject and receives the plunger or piston member 16, while the spring 20 serves to bias the barrel 14 into the position illustrated by FIG. 2.

Figures 3, 7, 8:
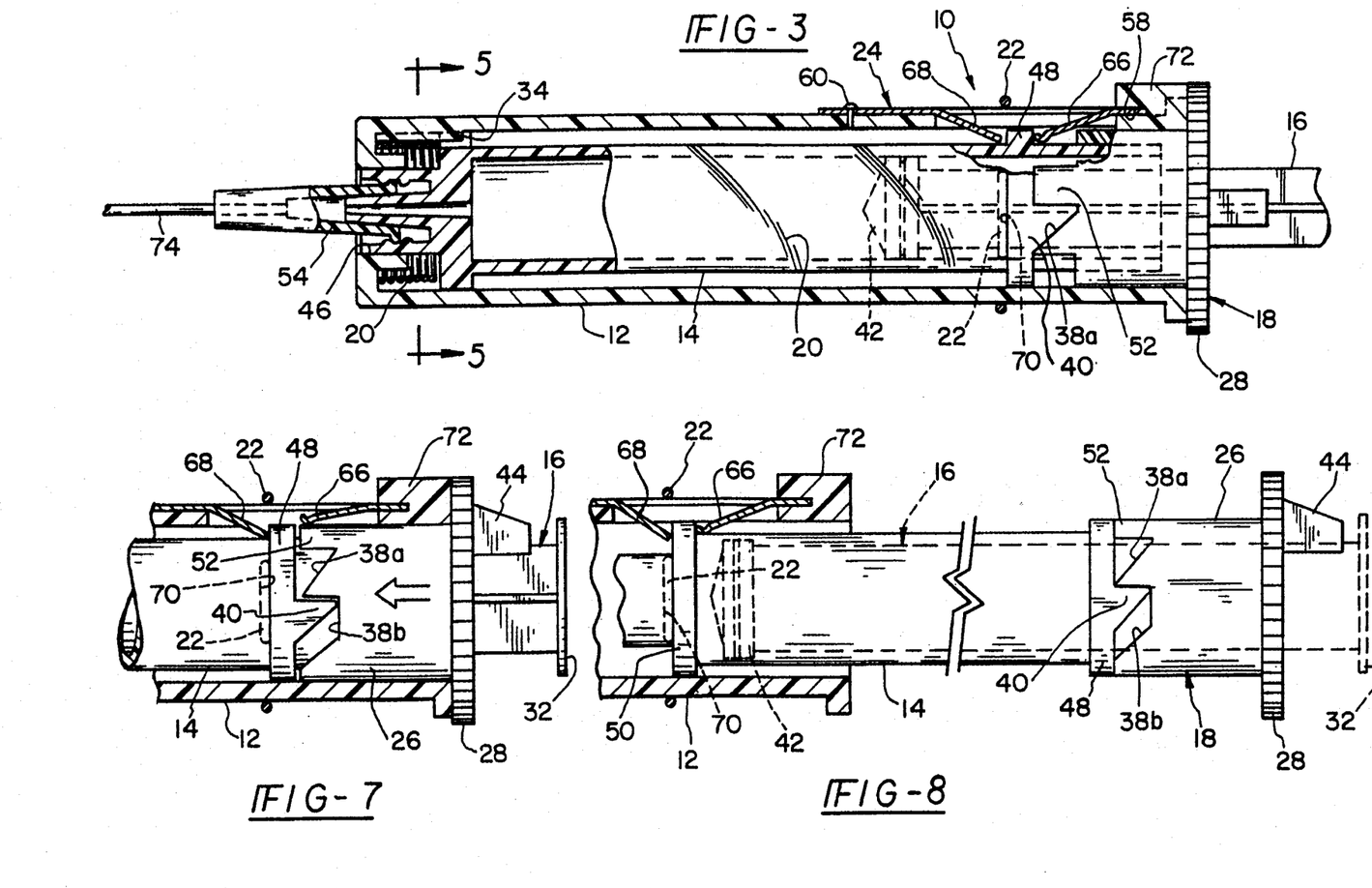
FIG. 3 is a cross sectional side view of the self-sheathing syringe assembly of FIG. 1.
FIGS. 6, 7 and 8 illustrate the sequential operation of the syringe assembly in accordance with the preferred embodiment of this invention.

With reference to FIG. 3, the syringe 10 is shown as a relatively compact assembly, with the individual components being substantially nested within each other. FIG. 3 shows the syringe 10 as it would likely be received by the user. The hypodermic needle 74 is shown as being mounted within a boss 54 formed on one end of the barrel 14, which is substantially telescoped within the sheath 12 such that the needle 74 projects through an aperture 46 in the corresponding end of the sheath 12. The spring 20 is axially compressed between the sheath 12 and the barrel 14, so as to urge the syringe barrel 14 in a direction which would retract the needle 74 into the sheath 12.

At the opposite end of the syringe 10, the camming member 18 is shown as having an annular camming portion 26 nested between the sheath 12 and the barrel 14, with only a radially extending flange 28 being visible from the exterior of the syringe 10. Located adjacent this end of the syringe 10 is the locking member 24 shown in FIGS. 1 and 2. The locking member 24 includes a deployment lock 66 which maintains the barrel 14 in the position shown in FIG. 3, so as to prevent the barrel 14 from being driven by the spring 20 to the position shown in FIG. 2. In addition, the locking member 24 includes a redeployment lock 68 which prevents the barrel 14 from being reinserted into the sheath 12 once it has reached the position shown in FIG. 2. Preferably, as seen in FIG. 4, the redeployment lock 68 is tapered and terminates in a sharp point, for a purpose to be explained below.

Figure 4:
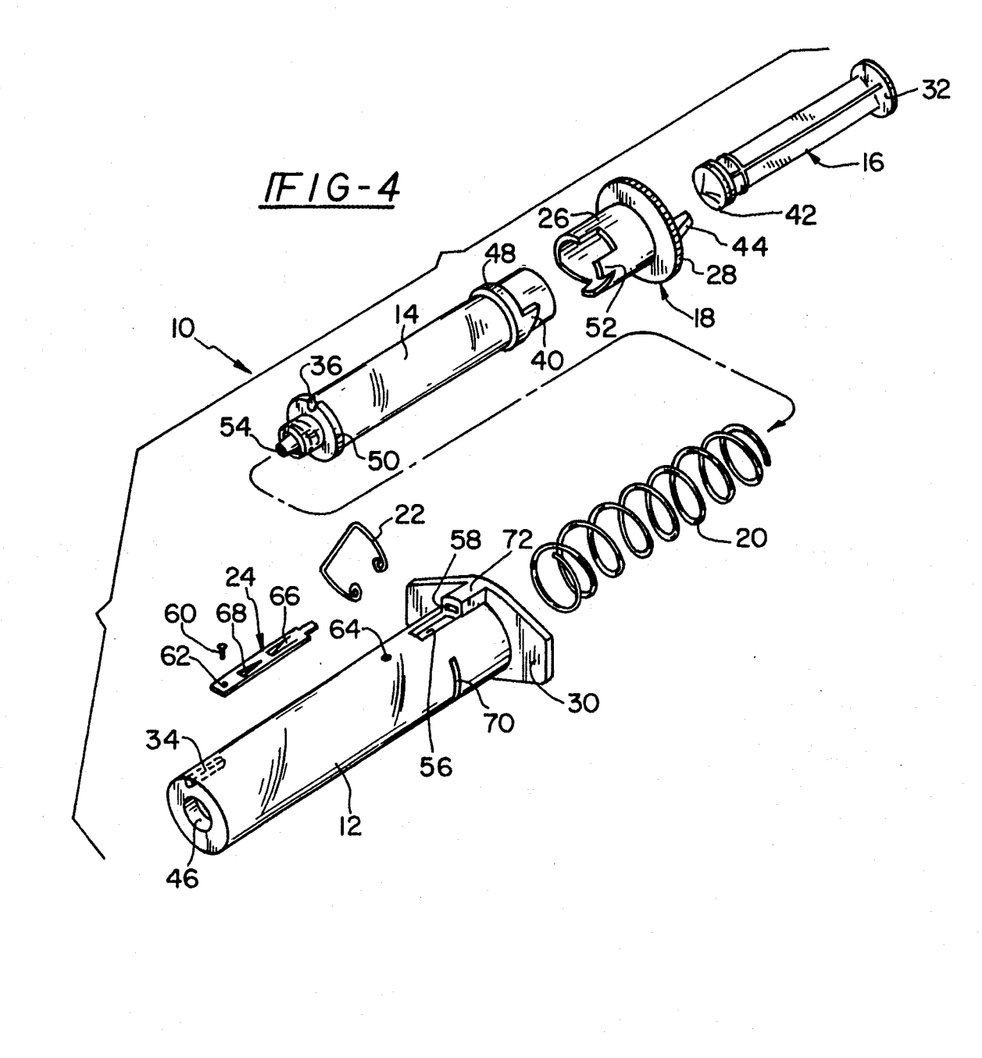
FIG. 4 is an exploded view of the self-sheathing syringe assembly of FIG. 1.

As can be seen in the exploded view of FIG. 4, the locking member 24 can be readily formed as a one piece metal stamping, with the deployment and redeployment locks 66 and 68 being cantilevered sections of the locking member 24. With the locking member 24 secured to the sheath 12, the deployment and redeployment locks 66 and 68 project through a longitudinal opening 56 formed in the sheath 12 and are resiliently biased against the barrel 14. As shown in FIG. 4, the locking member 24 is secured to the sheath 12 by inserting one end of the locking member 24 into a recess 58 formed in a boss 72 on the sheath 12, and securing the other end of the locking member 24 to the sheath 12 with a suitable fastener 60 inserted through a hole 62 in the locking member 24 and into a blind hole 64 formed in the sheath 12.

With reference again to FIG. 3, the deployment lock 66 is shown as being engaged with an annular rear abutment 48 formed on the periphery of the barrel 14. With the deployment lock 66 in this position, the barrel 14 cannot be axially displaced from the position shown in FIG. 3. Further insertion of the barrel 14 into the sheath 12 is prevented by the snap ring 22. As more clearly seen in the exploded view of FIG. 4, the snap ring 22 projects through a groove 70 formed through the wall of the sheath 12 so as to engage the shoulder of the rear abutment 48 opposite to that engaged by the deployment lock 66.

Figures 5, 6:
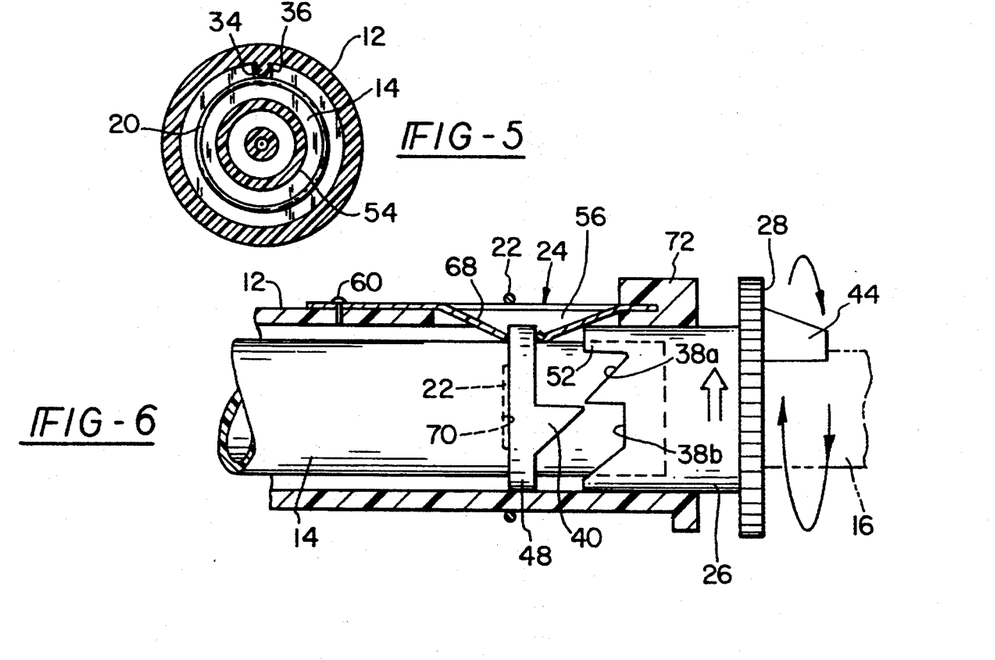
FIG. 5 is a cross sectional view of the self-sheathing syringe assembly along line 5—5 of FIG. 3.

Some of the remaining internal features and components of the syringe 10 can be more clearly seen with further reference to FIG. 4. The barrel 14 includes an annular front abutment 50 adjacent the boss 54 for receiving the hypodermic needle 74. On the periphery of the front abutment 50 is a radial slot 36, which corresponds to an axial rib 34 formed on the interior wall of the sheath 12 adjacent the aperture 46. As can be seen in FIG. 5, the axial rib 34 serves to align the barrel 14 with the sheath 12 by engaging the radial slot 36 when the barrel 14 is completely inserted within the sheath 12, as shown in FIG. 3. By maintaining this alignment, the barrel 14 is prevented from rotating relative to the sheath 12 while the camming member 18 is rotated, the purpose of which will be described below.

At the opposite end of the barrel 14, and shown as a longitudinal projection from the rear abutment 48, a cam follower 40 is shown as being integrally formed with the main body of the barrel 14. The cam follower 40 cams with camming slots 38a and 38b, shown in greater detail in FIGS. 6 through 8, which are formed on the annular camming portion 26 of the camming member 18. The camming member 18 also includes a release tab 52 which engages the deployment lock 66 when the camming member 113 is properly indexed relative to the barrel 14. The camming member 18 rotatably circumscribes the end of the barrel 14 adjacent the rear abutment 48. The plunger 16 is reciprocably disposed in the barrel or outer member 14, and includes a piston or syringe 42 formed or secured on the end of the plunger 16 received within the barrel 14.

With the above description, the use and operation of the syringe 10 of this invention will be described with reference to FIGS. 3 and 6 through 8. FIG. 3 shows the cam follower 40 engaged with the first cam slot 38a prior to use of the syringe 10. Furthermore, FIG. 3 shows the plunger 16 as being partially withdrawn from the barrel 14, in a position which corresponds to medication having been drawn from a suitable source (not shown) into the barrel 14. The deployment lock 66 is shown engaged with the rear abutment 48 of the barrel 14 to prevent the needle 74 from being retracted into the sheath 12. As also indicated in FIG. 3, the release tab 52 is angularly displaced from the deployment lock 66.

FIG. 6 illustrates the manner in which the syringe 10 is prepared for the injection procedure. The camming member 18 is indexed by grasping and rotating the flange 28 in the direction indicated by the arrows. The contour of the cam slot 38a prevents the catching member 18 from being accidently rotated in the opposite direction. FIG. 7 illustrates the placement of the cam follower 40 within the second cam slot 38b immediately prior to and during the step in which the contents of the barrel 14 are injected. Importantly, with the cam follower 40 engaged with the second cam slot 38b, the release tab 52 has been indexed beneath the deployment lock 66, as shown. That the deployment lock 66 is aligned with the release tab 52 can be confirmed by an alignment tab 44 which projects longitudinally from the flange 28 of the camming member 18. As can be clearly seen in FIG. 7, the deployment lock 66 has been raised sufficiently such that the rear abutment 48 of the barrel 14 can now pass beneath the deployment lock 66. Accordingly, the barrel 14 automatically telescopes outwardly relative to the sheath 12 as soon as the user releases the syringe 10, as is shown in FIG. 8. The syringe 10 now has the appearance of that shown in FIG. 2, with the needle 74 being completely and safely retracted within the sheath 12.

Figure 9:
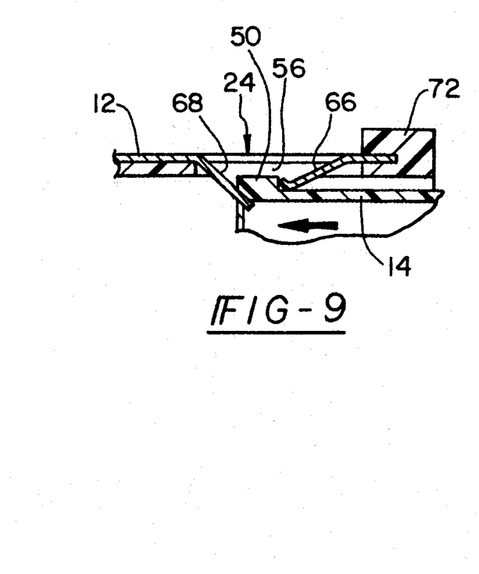
FIG. 9 is a cross sectional side view of the self-sheathing syringe assembly which shows in detail the manner in which the syringe assembly is disabled if an attempt is made to reuse the assembly.

FIG. 8 illustrates the permanent disabling mode of the syringe 10 after the syringe 10 has been used. Under the influence of the spring 20, the barrel 14 is now projecting from the rear of the sheath 12, with only the snap ring 22 preventing the barrel 14 from being completely ejected from the sheath 12. The redeployment lock 68 is now resting on the front abutment 50 of the barrel 14. However, as shown in FIG. 9, any effort to re-install the barrel 14 within the sheath 12 so as to redeploy the needle 74 will cause the redeployment lock 68 to pierce the wall of the barrel 14, rendering the syringe 10 completely and permanently unusable.

As can be seen from the above, a significant advantage of the present invention is that a single-use, self-sheathing hypodermic syringe 10 is provided which can be used in a substantially conventional manner. Essentially, the only additional step to activating the self-sheathing operation of the syringe 10 is to index the camming member 18 prior to injection. By eliminating the requirement to manually disable the syringe 10 after injection, the syringe 10 of this invention permits the user to tend to the recipient of the injection immediately after the injection procedure, instead of being concerned for the hazard posed by the hypodermic needle 74. Furthermore, the syringe 10 is made safe immediately and automatically after its use, without any further action from the user, such that accidental scratching or cutting of the user or others is practically impossible.

In addition, once the hypodermic needle 74 is completely and safely withdrawn into the sheath 12, the redeployment lock 68 prevents the hypodermic needle 74 from being redeployed outside of the sheath 12. In fact, any effort to reinsert the barrel 14 into the sheath 12 causes the redeployment lock 68 to pierce the barrel 14, rendering the syringe 10 useless.

Another significant advantage of the present invention is that the locking mechanism of the syringe 10 is uncomplicated, cannot be easily defeated, and does not require the entire contents of the syringe 10 to be used before the syringe 10 can be disabled. The syringe 10 also has a distinctive appearance when disabled, such that with a casual visual inspection the syringe 10 can quickly be identified by the user and others as being previously used.

Furthermore, the advantages of the syringe 10 of this invention can be realized with relatively few components, each of which can be readily manufactured using mass production methods. Accordingly, the syringe 10 of this invention can be assembled with relative ease, and the syringe 10 substantially has the outward appearance of a conventional syringe. In addition, the internal capacity of the barrel 14 is not diminished by a requirement for internal components disposed within the barrel 14. Such a requirement would also expose such internal components to the contents of the barrel 14, which could serve as additional sources of contamination for the contents of the syringe 10.

While the invention has been described in terms of a preferred embodiment, it is apparent that other forms could be adopted by one skilled in the art. For example, the structure of the camming member 18 could be modified, as well as the shape of the cam follower 40 and the cam slots 38a and 38b, the barrel 14 could be aligned relative to the sheath 12 with other suitable alignment features, and other suitable features or components could be substituted for the snap ring 22, the abutments 48 and 50, the locking member 24 and the spring 20. Accordingly, the scope of the invention is to be limited only by the following claims.

What is claimed is:

1. A self-sheathing syringe assembly comprising:
   a syringe having an outer tube, a piston member mounted within said outer tube for movement relative thereto, and means for sealingly engaging said piston member to said outer tube, said outer tube having an apertured end for receiving a needle and an oppositely disposed open end;
   sheathing means having one end slidably mounted to said apertured end of said outer tube of said syringe, and an oppositely disposed open end;
   means disposed at said apertured end of said outer tube for receiving a needle;
   a camming member rotatably mounted to said opposite end of said outer tube, said camming member further disposed between said outer tube of said syringe and said sheathing means proximate said open end, said camming member further having a first portion defining a camming contour at one end and a second portion defining a means for releasing said outer tube of said syringe for movement relative to said sheathing means;

means disposed on said outer tube for camming against said camming contour of said first portion of said camming member;

first means for locking said outer tube in a predetermined locked position, said first locking means being mounted to said sheathing means and being engagable with said outer tube for maintaining said outer tube in said predetermined locked position;

means for biasing said outer tube in a direction away from said one end of said sheathing means, said biasing means being mounted contiguous said apertured end of said outer tube and said one end of said sheathing means so as to bias said first locking means whereby as said releasing means of said second portion of said camming member is moved in a first predetermined direction for dispensing the contents of said syringe, said releasing means communicates with said first locking means to disengage said outer tube from said first locking means such that said outer tube and associated needle under the influence of said biasing means shuttles said outer tube from said predetermined locked position to a retracted position within said sheathing means; and second locking means mounted to said sheathing means for maintaining said outer tube of said syringe in said retracted position, said second locking means further comprising means for puncturing said outer tube;

whereby any attempt to move said outer tube from said retracted position to said predetermined locked position results in said puncturing means puncturing said outer tube so as to prevent reuse of said syringe.

2. The self-sheathing syringe assembly of claim 1 wherein said camming member is supported on said outer tube so as to be rotatable about a longitudinal axis of said outer tube.

3. The self-sheathing syringe assembly of claim 1 further comprising means associated with said outer tube for angularly aligning said outer tube with said sheathing means.

4. The self-sheathing syringe assembly of claim 1 further comprising means mounted to said outer tube for preventing said outer tube from being disengaged from said sheathing means.

5. The self-sheathing syringe assembly of claim 1 further comprising abutment means formed on said outer tube for engaging said first locking means when said outer tube is in said predetermined locked position, said camming member being rotatably supported on said outer tube so as to abut said abutment means.

6. The syringe assembly of claim 1 wherein said camming contour comprises a first detent corresponding to said predetermined locked position of said outer tube, and a second detent corresponding to said second position of said outer tube.

7. The self-sheathing syringe assembly of claim 1 further comprising a hypodermic needle received within said needle receiving means.

8. A self-sheathing means syringe assembly comprising:

tubular-shaped sheathing means having an open end and an aperture formed in an oppositely disposed end;

a tubular-shaped outer tube member telescopically engaged with said sheathing means, said outer tube member having an open end and an oppositely disposed apertured end, said outer tube member having an abutment proximate said open end;

means disposed at said apertured end of said outer tube member for receiving a needle;

means associated with said outer tube member for angularly aligning said outer tube member with said sheathing means;

means engaged with said outer tube member for preventing said outer tube member from being disengaged from said sheathing means;

a camming member rotatably supported on said open end of said outer tube member adjacent said abutment, said camming member further disposed between said outer tube member and said sheathing means proximate said open end, said camming member further having a first portion defining a camming contour at one end and a second portion defining a means for releasing said outer tube member of said syringe for movement relative to said tubular-shaped sheathing means, said camming contour having a first detent and a second detent;

means formed on said outer tube member for camming against said camming contour of said first portion of said camming member;

first means for locking said outer tube member in a predetermined locked position, said first locking means being mounted to said tubular-shaped sheathing and being engagable with said outer tube member for maintaining said outer tube member in said predetermined locked position wherein said needle receiving means of said outer tube member is adjacent and extending in a direction protecting from said apertured end of said tubular-shaped sheathing means;

means for biasing said outer tube member in a direction away from said apertured end of said tubular-shaped sheathing means, said biasing means being mounted contiguous said apertured end of said outer tube member and said apertured end of said tubular shaped sheathing means so as to bias said first locking means whereby as said releasing means of said camming member is moved in a first predetermined direction for dispensing the contents of said syringe, said releasing means communicates with said first locking means to disengage said outer tube member from said first locking means such that said outer tube member and associated needle under the influence of said biasing means shuttles said outer tube member from said predetermined locked position to a retracted position within said tubular-shaped sheathing means; and second locking means mounted to said tubular-shaped sheathing means for maintaining said outer tube member in said retracted position wherein said needle receiving means of said outer tube member is axially displaced from said apertured end of said tubular-shaped sheathing means, said second locking means further comprising means for puncturing said outer tube;

such that rotation of said camming member relative to said outer tube member causes said camming means to disengage said first detent and engage said second detent for dispensing the contents of the syringe, whereafter said releasing means disengages said first means for locking from said outer tube member such that said outer tube member shuttles from said predetermined locked position to said retracted position and any further attempt to shuttle said outer tube member back to said predetermined locked position activates said puncturing means to puncture said outer tube member so as to prevent reuse of said syringe.

9. The self-sheathing syringe assembly of claim 8 wherein said camming member is rotatable about a longitudinal axis of said outer tube member.

10. The self-sheathing syringe assembly of claim 8 wherein said alignment means comprises a slot formed in said outer tube member and a longitudinal rib formed on said sheathing means.

11. The self-sheathing syringe assembly of claim 8 wherein said means engaged with said outer tube member for preventing said outer tube member from disengaging said tubular-shaped sheathing means comprises a retaining member, said retaining member abutting said abutment when said outer tube member is in said predetermined locked position, said retaining member abutting said apertured end of said outer tube member when said outer tube member is in said retracted position.

12. The self-sheathing syringe assembly of claim 8 wherein said abutment engages said first locking means when said outer tube member is in said predetermined locked position.

13. The self-sheathing syringe assembly of claim 8 wherein said camming member comprises an annular member, said first portion of said camming contour being a saw-toothed profile formed on said annular member.

14. The self-sheathing syringe assembly of claim 8 further comprising a hypodermic needle received within said needle receiving means of said outer tube member.

15. The self-sheathing syringe assembly of claim 8 wherein said first locking means is a cantilevered member biased against said outer tube member so as to engage said abutment when said outer tube member is in said predetermined locked position.

16. The self-sheathing syringe assembly of claim 8 wherein said second locking means is a cantilevered member biased against said outer tube member.

17. The self-sheathing syringe assembly of claim 16 wherein said means for puncturing is located on said cantilevered member for piercing said outer tube member when said outer tube member is urged from said retracted position toward said predetermined locked position.

18. The self-sheathing syringe assembly of claim 8 wherein said biasing means is a compression spring disposed within said sheathing means so as to bias against said apertured end of said outer tube member.

* * * * *

UNITED STATES PATENT AND TRADEMARK OFFICE
CERTIFICATE OF CORRECTION

PATENT NO. : 5,433,712
DATED : July 31, 1995
INVENTOR(S) : Donald E. Stiles, Randall M. Brakeman and Dewayne J. Sherwin It is certified that error appears in the above-indentified patent and that said Letters Patent is hereby corrected as shown below:

Column 1, line 44, delete "," insert ---- . ----.

Column 7, line 2, delete "113" insert ---- 18 ----.

Column 7, line 6, delete "member" insert ---- tube ----.

Column 7, line 7, delete "syringe" insert ---- inner tube ----.

Column 7, line 27, delete "catching" insert ---- camming ----.

Column 9, line 64, delete ---- means ----.

Column 10, line 31, after "sheathing" insert ---- means ----.

Column 10, line 35, delete "protecting" insert ---- projecting ----.

UNITED STATES PATENT AND TRADEMARK OFFICE
CERTIFICATE OF CORRECTION

PATENT NO. : 5,433,712
DATED : July 31, 1995
INVENTOR(S) : Donald E. Stiles, Randall M. Brakeman and Dewayne J. Sherwin It is certified that error appears in the above-indentified patent and that said Letters Patent is hereby corrected as shown below:

```
Column 10, line 43, after "tubular" insert ---- - ----.

Column 11, line 15, after "said" insert ---- tubular-shaped ----.

Column 12, line 26, after "said" insert ---- tubular-shaped ----.
```

Signed and Sealed this

Nineteenth Day of September, 1995

*Attest:*

BRUCE LEHMAN

*Attesting Officer*  *Commissioner of Patents and Trademarks*